United States Patent
Schrempf et al.

[11] Patent Number: 5,958,454
[45] Date of Patent: Sep. 28, 1999

[54] EFFERVESCENT BATH TABLET COMPOSITIONS

[75] Inventors: David O. Schrempf, Los Angeles, Calif.; Ward M. Smith, Mystic, Conn.

[73] Assignee: R&D Ventures, Inc., Los Angeles, Calif.

[21] Appl. No.: 08/866,030

[22] Filed: May 30, 1997

Related U.S. Application Data

[60] Provisional application No. 60/018,812, May 31, 1996.

[51] Int. Cl.$^6$ ....................................................... A61K 9/46
[52] U.S. Cl. ............................................ 424/466; 514/784
[58] Field of Search ............................................... 424/466

[56] References Cited

U.S. PATENT DOCUMENTS

| | | | |
|---|---|---|---|
| 4,417,993 | 11/1983 | Gergely | 252/90 |
| 4,650,667 | 3/1987 | Eguchi et al. | 424/44 |
| 4,666,707 | 5/1987 | Eguchi et al. | 424/44 |
| 4,897,257 | 1/1990 | Nishikawa et al. | 424/44 |
| 5,002,758 | 3/1991 | Ichii et al. | 424/44 |
| 5,055,305 | 10/1991 | Young | 424/466 |
| 5,286,492 | 2/1994 | Dettmar et al. | 424/458 |

FOREIGN PATENT DOCUMENTS

| | | |
|---|---|---|
| 47798/72 | 5/1975 | Australia . |
| 1365024 | 8/1974 | United Kingdom . |

*Primary Examiner*—Thurman K. Page
*Assistant Examiner*—James M. Spear
*Attorney, Agent, or Firm*—Pretty, Schroeder & Poplawski, P.C.

[57] ABSTRACT

The present invention relates to effervescent bath tablet compositions that contain an organic acid, sodium bicarbonate, sodium carbonate, and a salt of a fatty acid. These invention bath tablet compositions characteristically exhibit low dissolution rates in warm water.

30 Claims, No Drawings

EFFERVESCENT BATH TABLET COMPOSITIONS

This application claims priority based upon Ser. No. 60/018,812 filed May 31, 1996.

FIELD OF THE INVENTION

The present invention relates to bath tablet compositions that effervesce in water.

BACKGROUND OF THE INVENTION

Bath additives such as bubble bath preparations and inorganic salts (e.g., sodium sulfate, borax, and sodium chloride) are primarily utilized for their various asthetic (e.g., fragrance, etc.) and purported cosmetic or therapeutic functions (e.g., moisturizing effect, soothing effect, etc.). These bath additives are typically developed for adults who are more likely to be attracted to products that exhibit these features. One of the effects of using these additives is that users are more likely to be motivated to prolong the duration of their baths. However, children are not as likely to be as impressed with these types of products as adults are. Therefore, these additives are not likely to have the same motivating effect on children as they have on adults.

Effervescent preparations have been described that contain an acid, a carbonate salt, and other agents that combine with water to produce cosmetic and therapeutic effects. The acid and carbonate salt combine in water to generate effervescent carbon dioxide bubbles. However, as these preparations purport to have a therapeutic effect, they may not be suitable for use with children. Moreover, these preparations dissolve relatively fast, thus decreasing the likelihood that the effervescent phenomena will captivate a child's attention for a prolonged period of time during a bath.

Accordingly, a need exists for effervescent bath compositions that are non-therapeutic, yet slow dissolving so that effervescent bubbles are generated in water over relatively long periods by using relatively small quantities of the compositions.

BRIEF DESCRIPTION OF THE INVENTION

In accordance with the present invention, effervescent bath tablet compositions are provided that characteristically exhibit low dissolution rates in warm water. Effervescent bath tablet compositions of the present invention contain an organic acid, sodium bicarbonate, sodium carbonate, and a salt of a fatty acid.

DETAILED DESCRIPTION OF THE INVENTION

In accordance with the present invention, there is provided a bath tablet composition containing:

a) an organic acid;
b) sodium bicarbonate;
c) sodium carbonate; and
d) a salt of a fatty acid, wherein a 0.01 percent by weight aqueous solution of said bath tablet composition has a pH of 7.0 or above.

As used herein, the term "bath tablet composition" refers to a composition that effervesces when added to water, such as, for example, bath water. Bath tablet compositions of the present invention exhibit characteristically long shelf life. Additionally, when added to water, these compositions dissolve slowly to maintain production of effervescent bubbles over a relatively long period of time.

The term "organic acid" refers herein to a carbon-containing acid. Organic acids that are suitable for use in the practice of the present invention are those that are capable of existing under ambient conditions in solid, particulate form. As used herein, the terms "particulate" and "particle(s)" refer to discrete solid units of material.

Exemplary carboxylic acids contemplated for use in the practice of the present invention include malonic acid, succinic acid, glutaric acid, adipic acid, pimelic acid, fumaric acid, maleic acid, phthalic acid,, glutamic acid, aspartic acid, glycolic acid, tartronic acid, malic acid, tartaric acid, hydroxybenzoic acid, citric acid, salicylic acid, tropic acid, ascorbic acid, cinnamic acid, phenylacetic acid, nicotinic acid, sorbic acid, trimellitic acid, and the like, as well as combinations of any two or more thereof.

Organic acids that are particularly useful in carrying out the practice of the invention contain up to about eight carbon atoms. Preferred organic acids include, for example, citric acid, tartaric acid, succinic acid, malic acid, and fumaric acid.

Compositions of the present invention typically contain from about 5 to about 50 weight percent organic acid, based on total composition weight. Preferably, the invention compositions contain from about 20 to about 40 weight percent organic acid, based on total composition weight. Most preferably, the invention compositions contain from about 20 to about 35 weight percent sodium organic acid, based on total composition weight.

The solid, particulate organic acids employed in the practice of the present invention can be of varying particle sizes. However, typically at least about 50 weight percent of the organic acid particles is within the particle size range of about 149 microns (i.e., #100 USS sieve) to about 1190 microns (i.e., #16 USS sieve). Preferably, at least about 80 weight percent of the organic acid particles is within the particle size range of about 149 microns (i.e., #100 USS sieve) to about 1190 microns (i.e., #16 USS sieve). Most preferably, at least about 90 weight percent of the organic acid particles is within the particle size range of about 149 microns (i.e., #100 USS sieve) to about 1190 microns (i.e., #16 USS sieve), where at least 45 weight percent of the organic acid particles is also within the particle size range of about 149 microns (i.e., #100 USS sieve) to about 595 microns (i.e., #30 USS sieve). Also preferred are compositions where at least 90 weight percent of the organic acid particles is within the particle size range of about 149 microns (i.e., #100 USS sieve) to about 1190 microns (i.e., #16 USS sieve), where at least 45 weight percent of the organic acid particles is also within the particle size range of about 297 microns (i.e., #50 USS sieve) and 1190 microns (i.e., #16 USS sieve).

Bath tablet compositions of the present invention also contain both sodium bicarbonate and sodium carbonate. Typically, relative quantities of sodium carbonate to sodium bicarbonate are selected so that the ratio of quantity of sodium carbonate to sodium bicarbonate is within the range of about 1 to about 3. Preferably, the ratio of quantity of sodium carbonate to sodium bicarbonate is within the range of about 1 to about 2.

The amount of sodium bicarbonate employed can vary, however, typical invention compositions contain from about 5 to about 50 weight percent sodium bicarbonate, based on the total composition weight. Preferably, invention compositions contain from about 10 to about 35 weight percent sodium bicarbonate, based on the total composition weight. Most preferably, compositions of the present invention contain from about 20 to about 30 weight percent sodium bicarbonate, based on the total composition weight.

It is not required that particles of sodium bicarbonate and sodium carbonate employed in the practice of the present invention be within a particular particle size range. However, a preferred sodium bicarbonate particle size distribution is where about 40 weight percent of the sodium bicarbonate particles (based on total weight of sodium bicarbonate employed) have particle sizes that are between about 149 microns (i.e., #100 USS sieve) and about 210 microns (i.e., #70 USS sieve). Most preferably, about 50 weight percent (based on total weight of sodium bicarbonate employed) of sodium bicarbonate particles is within the particle size range of about 149 microns (i.e., #100 USS sieve) and about 210 microns (i.e., #70 USS sieve).

Compositions of the present invention typically contain from about 5 to about 50 weight percent sodium carbonate, based on the total composition weight. Preferably, the invention compositions contain from about 20 to about 45 weight percent sodium carbonate, based on the total composition weight. Most preferably, the invention compositions contain from about 25 to about 40 weight percent sodium carbonate, based on the total composition weight.

Bath tablet compositions of the present invention also contain one or more fatty acids, in salt form. Salts employed in the practice of the present invention contain a metal cation and one or more anionic fatty acid groups. The metal cations typically are a mono-, di-, or tri-valent metal cation, such as, for example, sodium, magnesium, aluminum, and the like. As used herein, the term "fatty acid group" refers to an acid that contains from about 8 to about 36 carbon atoms. Preferably the fatty acid group contains from about 12 to about 22 carbon atoms.

The number of anionic fatty acid groups associated with each cation depends on the valency of the cationic group. For example, a monovalent cation, such as, for example, a sodium ion, will associate with one anionic fatty acid group. Similarly, a divalent cation, such as, for example, a magnesium ion, will associate with two anionic fatty acid groups, and a trivalent cation, such as, for example, an aluminum ion, will associate with three anionic fatty acid groups.

Fatty acid groups contemplated for use in the practice of the present invention may be saturated or unsaturated. Suitable fatty acid groups include lauric acid, palmitic acid, stearic acid, and the like, as well as combinations of two or more thereof. Typically, bath tablet compositions of the present invention contain from about 0.001 to about 5 weight percent of a salt of a fatty acid, based on total composition weight. Preferably, the invention bath tablet compositions contain from about 0.01 to about 1 weight percent of the fatty acid, in salt form, based on total composition weight. Most preferably, the invention bath tablet compositions contain from about 0.05 to about 0.5 weight percent of the fatty acid, in salt form, based on total composition weight.

Optionally, invention compositions can also contain sodium benzoate. When sodium benzoate is employed as a component in compositions of the present invention, typically from about 0.01 to about 10 weight percent sodium benzoate is employed, based on total composition weight. Preferably, from about 0.1 to about 5 weight percent sodium benzoate is employed, based on total composition weight. Most preferably, from about 0.5 to about 3 weight percent sodium benzoate is employed, based on total composition weight.

Bath tablet compositions of the present invention exhibit superior performance with respect to their relatively long shelf life and the relatively low dissolution rate of the invention compositions in water. The low dissolution rate of the invention bath tablet compositions functions to prolong the time period during which effervescent bubbles are produced. Typically, invention bath tablet compositions exhibit a dissolution rate of less than about 0.5 grams per second, as measured in distilled water maintained at 40° C. Preferably, bath tablet compositions of the present invention exhibit a dissolution rate of less than about 0.1 grams per second, as measured in distilled water maintained at 40° C. Most preferably, invention bath tablet compositions exhibit a dissolution rate of less than about 0.05 grams per second, as measured in distilled water maintained at 40° C.

Aqueous solutions containing bath tablet compositions of the present invention are characteristically alkaline. For example, a 0.01 percent by weight, aqueous solution of the invention bath tablet compositions has a pH that is typically 7.0 or above. The pH of aqueous solutions containing 0.01 weight percent of preferred bath tablet compositions is typically within the pH range of about 7.5 to about 9.0. The pH of aqueous solutions containing 0.01 weight percent of the most preferable bath table compositions is typically within the pH range of about 7.5 to about 8.0.

Bath tablet compositions of the present invention can be pressed into a variety of shapes and sizes using tabletting methods that are well known to those of ordinary skill in the art, such as, for example, wet granulation or direct compression. Invention compositions can also contain optional additives, such as, for example, asthetic agents (e.g., coloring agents, fragrance agents, etc.), excipients (e.g., sorbitol, lactose, and the like, and mixtures of any two or more thereof), binding agents (e.g., gelatin, polyvinyl alcohol, etc.), lubricants (e.g., polyethylene glycol, sodium benzoate, etc.), and the like, as well as combinations of any two or more thereof. Suitable quantities of these components can be readily determined by those of ordinary skill in the art.

The invention will now be described in greater detail with reference to the following non-limiting example.

EXAMPLE

A 1 kilogram batch of invention bath tablet composition was prepared by mixing together the following:

1) 11.88% by weight "Citric Acid Anydrous USP/FCC G" (anhydrous citric acid with the following particle size distribution: 5% maximum on #16 USS sieve (1190 micrometers), 5% maximum through a #50 USS sieve (297 micrometers)) (Ashland Chemical Co., Columbus, Ohio);

2) 11.88% by weight "Citric Acid Anhydrous USP/FCC FG" (anhydrous citric acid with the following particle size distribution: 3% maximum on #30 USS sieve (595 micrometers), 5% maximum through #100 USS sieve (149 micrometers)) (Ashland Chemical Co., Columbus, Ohio);

3) 22.76 % by weight of sodium bicarbonate (Church & Dwight Co., Inc., Princeton, N.J.);

4) 35.42% by weight soda ash (i.e., sodium carbonate) (FMC Wyoming Corp., Philadelphia, Pa.);

5) 0.86% by weight Blue Dye #2;

6) 11.00% by weight sorbitol (SPI Polyols, Inc. New Castle, Del.);

7) 3.00% by weight Carbowax 8000 (polyethylene glycol, molecular weight 8000) (Union Carbide, Danbury, Conn.);

8) 0.10% by weight fragrance;

9) 2.00% by weight sodium benzoate (Pfizer, New York, N.Y.); and 10) 0.10% magnesium stearate (Mallinckrodt, Chesterfield, Mo.).

The composition was pressed into 7 gram tablets using methods that are well known in the art.

The pH of a 0.01% by weight aqueous solution of this bath tablet composition was measured as 7.94. The dissolution rate of this composition was also measured by determining the amount of time required to completely dissolve one tablet (determined visually) in 5 liters of distilled water maintained at 40° C. A dissolution rate was computed in units of grams/seconds to dissolve. The dissolution rate for this composition was 0.071 grams/sec.

The above described composition and related pH and dissolution rate values are represented in column one of Table I presented below. Columns 2 through 4 provide illustrations of three other invention compositions and the related pH and dissolution rate values.

TABLE I

Bath Tablet Compositions In Weight Percent

| Component | 1 | 2 | 3 | 4 |
| --- | --- | --- | --- | --- |
| Citric Acid, G | 11.88 | 11.39 | 11.90 | 11.95 |
| Citric Acid, FG | 11.88 | 11.39 | 11.90 | 11.94 |
| Sodium Bicarbonate | 22.76 | 22.78 | 23.79 | 23.79 |
| Sorbitol | 11.00 | 11.00 | 11.00 | 11.00 |
| Carbowax 8000 | 3.00 | 3.00 | 3.00 | 3.00 |
| Magnesium Stearate | 0.10 | 0.10 | 0.10 | 0.10 |
| Sodium Benzoate | 2.00 | 2.00 | 2.00 | 2.00 |
| Dye | 0.86 | 4.26 | 0.73 | 0.64 |
| Fragrance | 0.10 | 0.10 | 0.10 | 0.10 |
| pH | 7.94 | 8.05 | 8.96 | 7.70 |
| Dissolution Rate (g/sec) | 0.07 | 0.05 | 0.04 | 0.05 |

Alternative Example

A 1 kilogram batch of invention bath tablet composition was prepared by mixing together the following:

1) 26.27% by wt. anhydrous citric acid;
2) 13.13% by wt. of sodium bicarbonate;
3) 34.50% by wt. soda ash (i.e., sodium carbonate);
4) 1.03% by wt. dye;
5) 24.635 by wt. lactose;
6) 0.08% sodium lauryl sulfate;
7) 0.03% sodium benzoate; and
8) 0.33% magnesium sterate.

The composition was pressed into 7 gram tablets using methods that are well known in the art. It has been found that this composition provides sufficient hardness, while reducing the stickiness of the tablet in the tablet press. Furthermore, this composition provides an active tablet and results in less residue in the bath.

While the invention has been described in detail with reference to certain preferred embodiments thereof, it will be understood that modifications and variations are within the spirit and scope of that which is described and claimed.

That which is claimed is:

1. A bath tablet composition comprising:
   a) an organic acid;
   b) sodium bicarbonate;
   c) from about 20 to about 45 percent sodium carbonate; and
   d) a salt of a fatty acid;
   wherein a 0.01 percent by weight aqueous solution of said bath tablet composition has a pH that is 7.0 or above.

2. The bath tablet composition according to claim 1, wherein said organic acid is selected from malonic acid, succinic acid, glutaric acid, adipic acid, pimelic acid, fumaric acid, maleic acid, phthalic acid, glutamic acid, aspartic acid, glycolic acid, tartronic acid, malic acid, tartaric acid, hydroxybenzoic acid, citric acid, salicylic acid, tropic acid, ascorbic acid, cinnamic acid, phenylacetic acid, nicotinic acid, sorbic acid, trimellitic acid, or combinations of any two or more thereof.

3. The bath tablet composition according to claim 2, wherein said organic acid is citric acid.

4. The bath tablet composition according to claim 1, wherein said fatty acid contains from about 8 to about 18 carbon atoms.

5. The bath tablet composition according to claim 1, wherein said fatty acid contains from about 12 to about 18 carbon atoms.

6. The bath tablet composition according to claim 1, wherein said salt is selected from sodium laurate or magnesium stearate.

7. The bath tablet composition according to claim 6 wherein said salt is magnesium stearate.

8. The bath tablet composition according to claim 1, further comprising sodium benzoate.

9. The bath tablet composition according to claim 1, wherein said pH is in the range of about 7.5 to about 8.0.

10. A bath tablet composition comprising:
    a) organic acid particles, wherein at least about 50 weight percent of said organic acid particles have a particle size within the range of about 149 microns to about 1190 microns;
    b) sodium bicarbonate particles;
    c) from about 20 to about 45 percent sodium carbonate particles; and
    d) a salt of a fatty acid;
    wherein a 0.01 percent by weight aqueous solution of said bath tablet composition has a pH that is 7.0 or above.

11. The bath tablet composition according to claim 10, wherein said organic acid particles are selected from particles of malonic acid, succinic acid, glutaric acid, adipic acid, pimelic acid, fumaric acid, maleic acid, phthalic acid,, glutamic acid, aspartic acid, glycolic acid, tartronic acid, malic acid, tartaric acid, hydroxybenzoic acid, citric acid, salicylic acid, tropic acid, ascorbic acid, cinnamic acid, phenylacetic acid, nicotinic acid, sorbic acid, trimellitic acid, or combinations of any two or more thereof.

12. The bath tablet composition according to claim 11, wherein said organic acid is citric acid.

13. The bath tablet composition according to claim 10, wherein said composition comprises from about 5 to about 50 weight percent of said organic acid.

14. The bath tablet composition according to claim 10, wherein said composition comprises from about 20 to about 40 weight percent of said organic acid.

15. The bath tablet composition according to claim 10, wherein said composition comprises from about 20 to about 35 weight percent of said organic acid.

16. The bath tablet composition according to claim 10, wherein said composition comprises from about 5 to about 50 weight percent of said sodium bicarbonate.

17. The bath tablet composition according to claim 10, wherein said composition comprises from about 10 to about 35 weight percent of said sodium bicarbonate.

18. The bath tablet composition according to claim 10, wherein said composition comprises from about 20 to about 30 weight percent of said sodium bicarbonate.

19. The bath tablet composition according to claim 10, wherein said pH is in the range of about 7.5 to about 8.0.

20. A bath tablet composition comprising:
   a) about 5 to about 50 weight percent citric acid particles, wherein at least about 50 weight percent of said citric acid particles have a particle size within the range of about 149 microns to about 1190 microns;
   b) about 5 to about 50 weight percent sodium bicarbonate;
   c) about 5 to about 50 weight percent sodium carbonate; and
   d) about 0.001 to about 5 weight percent magnesium stearate;
   e) about 0.01 to about 10 weight percent sodium benzoate, wherein all weight percents are based on total composition weight,
   wherein a 0.01 by weight aqueous solution of said bath tablet composition has a pH of 7.0 or above, and
   wherein said composition exhibits a dissolution rate of less than about 0.1 grams per second in water at 40° C.

21. The bath tablet composition according to claim 10, wherein said composition comprises from about 25 to about 40 weight percent of said sodium carbonate.

22. The bath tablet composition according to claim 10, wherein said composition comprises from about 0.001 to about 5 weight percent of said salt.

23. The bath tablet composition according to claim 10, wherein said composition comprises from about 0.01 to about 0.1 weight percent of said salt.

24. The bath tablet composition according to claim 10, wherein said composition comprises from about 0.05 to about 0.5 weight percent of said salt.

25. The bath tablet composition according to claim 10, wherein said fatty acid that contains from about 8 to about 22 carbon atoms.

26. The bath tablet composition according to claim 10, wherein said fatty acid contains from about 8 to about 12 carbon atoms.

27. The bath tablet composition according to claim 10, wherein said salt is magnesium stearate.

28. The bath tablet composition according to claim 10, wherein said bath tablet composition has a dissolution rate that is less than about 0.5 grams per second in water at 40° C.

29. The bath tablet composition according to claim 10, wherein said bath tablet composition has a dissolution rate that is less that about 0.1 grams per second in water at 40° C.

30. The bath tablet composition according to claim 10, wherein said bath tablet composition has a dissolution rate that is less that about 0.05 grams per second in water at 40° C.

* * * * *